(12) United States Patent
Bevinakatti et al.

(10) Patent No.: US 10,266,486 B2
(45) Date of Patent: Apr. 23, 2019

(54) METHOD OF MAKING A COMPOSITION OF AN ALKANOLAMINE ALKYLAMIDE AND A POLYOL

(71) Applicant: Akzo Nobel Chemicals International B.V., Arnhem (NL)

(72) Inventors: Hanamanthsa Bevinakatti, Somerset, NJ (US); Karen Lee White, Bridgewater, NJ (US)

(73) Assignee: AKZO NOBEL CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 16/070,326

(22) PCT Filed: Sep. 13, 2016

(86) PCT No.: PCT/EP2016/071554
§ 371 (c)(1),
(2) Date: Jul. 16, 2018

(87) PCT Pub. No.: WO2017/129272
PCT Pub. Date: Aug. 3, 2017

(65) Prior Publication Data
US 2019/0031598 A1    Jan. 31, 2019

Related U.S. Application Data

(60) Provisional application No. 62/289,010, filed on Jan. 29, 2016.

(51) Int. Cl.
| | | |
|---|---|---|
| *C07C 231/02* | (2006.01) | |
| *C07C 303/22* | (2006.01) | |
| *C07D 209/12* | (2006.01) | |
| *C07D 307/68* | (2006.01) | |
| *C07C 29/00* | (2006.01) | |
| *C07C 31/22* | (2006.01) | |
| *C07C 233/18* | (2006.01) | |

(52) U.S. Cl.
CPC ............ *C07C 231/02* (2013.01); *C07C 29/00* (2013.01); *C07C 31/225* (2013.01); *C07C 233/18* (2013.01)

(58) Field of Classification Search
CPC ... C07C 231/02; C07C 303/22; C07C 233/18; C07C 309/18; C07C 233/69; C07C 233/21; C07D 307/68; C07D 209/18; C07D 209/12
See application file for complete search history.

(56) References Cited

U.S. PATENT DOCUMENTS

| | | |
|---|---|---|
| 4,143,159 A | 3/1979 | Moller et al. |
| 4,851,434 A | 7/1989 | Deckner |
| 7,666,396 B2 | 2/2010 | Lange et al. |
| 7,816,310 B2 | 10/2010 | Landa et al. |
| 8,795,697 B2 | 8/2014 | Brown |
| 2003/0130636 A1 | 7/2003 | Brock et al. |
| 2005/0058674 A1 | 3/2005 | Joseph et al. |
| 2005/0058693 A1 | 3/2005 | Joseph et al. |
| 2005/0101927 A1 | 3/2005 | Joseph et al. |
| 2005/0113268 A1 | 5/2005 | Landa et al. |
| 2005/0271595 A1 | 12/2005 | Brown |
| 2012/0277444 A1 | 11/2012 | Mahadevan et al. |

FOREIGN PATENT DOCUMENTS

| | | |
|---|---|---|
| EP | 1 535 607 A1 | 6/2005 |
| EP | 1 455 722 B2 | 12/2011 |
| GB | 1 554 251 A | 10/1979 |
| GB | 1 589 224 A | 5/1981 |
| JP | 2000-327551 A | 11/2000 |
| JP | 2007-137786 A | 6/2007 |
| JP | 5334511 B2 | 8/2013 |
| WO | 2004/022115 A1 | 3/2004 |
| WO | 2004/022116 A1 | 3/2004 |
| WO | 2004/022117 A1 | 3/2004 |
| WO | 2017/129273 A1 | 8/2017 |
| WO | 2017/129274 A1 | 8/2017 |

OTHER PUBLICATIONS

Notification of Transmittal of the International Search Report and the Written Opinion of the International Searching Authority, or the Declaration from the International Bureau of WIPO for International Application No. PCT/EP2016/071554 dated Nov. 11, 2016.
Krakowiak et al., "A New Building Block Method to Synthesize Symmertrical and Asymmetrical Per-N-alkyl-Substituted Polyaza-Crown Compounds," vol. 54, No. 17, 1989, pp. 4061-4067, XP055308514.
Lange et al., "The homologs of monoethanolamine," Bulletin de la Societe Chimique de France (1951) 340-1, Abstract only.
Khanina et al., "Oxyethylation of amides of aliphatic low molecular acids as an experimental approach to obtaining new nontoxic cryoprotectants," Problemy Kriobiologii (1994), (3), 30-5, Institut Problem Kriobiologii i Kriomeditsiny NAN Ukrainy, Abstract only.
Ratchford, "N-Hydroxyalkyl amides of lactic acid. Preparation and properties," Industrial and Engineering Chemistry (1950), 42, 1565-7, Abstract only.
Anonymous: Technical Bulletin, Amides From Diglycolamine® Agent Diglycolamine® Agent [CAS 929-06-06], Jan. 1, 2007, XP055308615.

*Primary Examiner* — Jafar F Parsa
(74) *Attorney, Agent, or Firm* — Sandra B. Weiss

(57) ABSTRACT

The disclosure generally provides methods for preparing compositions comprising alkanolamine alkylamides and polyols. This disclosure further relates to methods for preparing compositions comprising alkanolamine alkylamides and polyols that can be used in formulations that provide moisturization.

14 Claims, No Drawings

METHOD OF MAKING A COMPOSITION OF AN ALKANOLAMINE ALKYLAMIDE AND A POLYOL

This application is a national stage filing under 35 U.S.C. § 371 of PCT/EP2016/071554, filed Sep. 13, 2016, which claims priority to U.S. Provisional Patent Application No. 62/289,010, filed Jan. 29, 2016, the contents of which are each incorporated herein by reference in their entireties.

BACKGROUND OF THE INVENTION

Field of the Invention

The disclosure generally provides methods for preparing compositions comprising alkanolamine alkylamides and polyols. This disclosure further relates to methods for preparing compositions comprising alkanolamine alkylamides and polyols that can provide moisturization when used in personal care formulations.

Description of Related Art

N-Acetylation of alkanolamines (also called aminoalcohols) to make acetamides is generally carried out by reacting alkanolamines with acetic anhydride, or with acetic acid, or with ethyl acetate, with or without catalysts. GB 1554251 discloses a process for preparing N-(2-hydroxyethyl)-acetamide (MEA Acetamide) using ethanolamine and excess ethyl acetate. After heating for 18 hours and distilling the product of the reaction twice under reduced pressure, the process gave about 66% yield for MEA Acetamide. US 2012/277444 also discloses the process for preparing MEA Acetamide from ethanolamine and a large excess of ethyl acetate. This process gave poor conversions and required the removal of excess ethyl acetate and work-up. Methods of preparing N-(2-(2-hydroxyethoxy)ethyl)-acetamide (DGA acetamide) are disclosed in Krakowiak et al., "A New Building Block Method To Synthesize Symmetrical and Asymmetrical Per-N-alkyl-Substituted Polyaza-Crown Compounds," *J. Org. Chem.*, 54(17): 4061-4067 (1989).

SUMMARY OF THE INVENTION

We recognized a need for a method for preparing alkanolamine alkylamides with improved efficiency and without forming unwanted byproducts. We observed that prior art methods have practical difficulties and give unwanted byproducts that must be removed from the product, especially when it is to be used as a humectant in personal care formulations meant for human use. For example, the N-acetylation with acetic anhydride produces acetic acid as a byproduct that must be removed before the composition can be formulated for personal care applications.

N-acetylation with acetic acid produces water as a byproduct. To drive the equilibrium of the reaction towards completion, the water must be removed, usually by distillation. But distillation of water leads to azeotrope formation with the reactant acetic acid, which also distills over with water. This results in the excessive usage of acetic acid and an inefficient process.

Finally, N-acetylation with ethyl acetate produces ethanol as a byproduct which must be removed by distillation to drive the reaction equilibrium to completion. Ethanol also forms an azeotrope with the reactant ethyl acetate, which also distills over with ethanol leading to excessive usage of ethyl acetate.

Another disadvantage of N-acetylation with ethyl acetate is that both ethanol and ethyl acetate cannot be used easily on a commercial scale production due to their low boiling and flash points. Therefore, this process is not preferred for commercial applications.

The method of the disclosure addresses the foregoing problems. It results in a composition (i.e., a mixture of a compound of formula (I) and a polyol) that has improved moisturization efficacy on skin and/or hair. Advantageously, the combination of the compound of formula (I) and the polyol can provide a synergistic relative moisturization efficacy. Thus, the combination has an increased moisturization efficacy over that expected and more than the sum of moisturization efficacies of the individual components alone.

In addition, the method of the disclosure can be performed with or without catalysts, and the product composition can be used without purification, distillation, or other work-up.

Furthermore, the process uses commercially available, relatively cheap, and safe polyol ester starting materials. Polyol ester compounds, such as triacetin (1,2,3-triacetoxypropane), can also be used as humectants in personal care formulations. Therefore, even if excess polyol ester compound is used in the process, it is not essential to remove it from the resulting product composition.

The methods of the disclosure generally relate to the following chemical reaction:

$$H\diagdown_O\diagdown^Z\diagdown_{NH_2} + \text{polyol ester} \longrightarrow H\diagdown_O\diagdown^Z\diagdown_N^H\diagdown^{C(O)R^1} + \text{polyol,}$$

wherein Z and $R^1$ are defined below.

Thus, one aspect of the disclosure provides methods of making a composition comprising
(i) a compound of formula (I)

$$H\diagdown_O\diagdown^Z\diagdown_N^H\diagdown^{C(O)R^1} \quad (I)$$

wherein
Z is (a) a linear or branched $C_2$-$C_6$ alkylene optionally substituted with one or more —OH or —($C_1$-$C_3$ alkyl)-OH, or (b) (—$R^2$—O—$R^3$—)$_n$, where n is an integer from 1 to 5, and each $R^2$ and $R^3$ is independently —$CH_2$—$CR^4H$—, wherein $R^4$ is H or an unsubstituted linear or branched $C_1$-$C_3$ alkyl; and
$R^1$ is an unsubstituted linear or branched $C_1$-$C_3$ alkyl;
and (ii) a polyol,
the method comprising reacting an alkanolamine of formula (II)

$$H\diagdown_O\diagdown^Z\diagdown_{NH_2} \quad (II)$$

with a polyol ester comprising at least one —C(O)$R^1$ moiety.

In another aspect, the disclosure provides a method of making a personal care formulation comprising mixing the composition that is the product of the method of the disclosure with other personal care formulation components, such as surfactants, thickeners, emulsifiers, preservatives, and the like. In some embodiments of this aspect, the product of the method of the disclosure is used directly, without being purified, distilled, or worked-up before being mixed with the other personal care formulation components.

In another aspect, the disclosure provides a personal care formulation comprising the reaction composition that is the product of the method of the disclosure.

In another aspect, the disclosure provides personal care formulations comprising the composition that is the reaction product of the method of the disclosure and one or more other personal care formulation components such as surfactants, thickeners, emulsifiers, preservatives, and the like. In some embodiments of this aspect, the personal care formulation comprises the composition that is the reaction product of the method of the disclosure that has not been purified, distilled, or worked-up.

In another aspect, the disclosure provides a method of moisturizing skin or hair, the method comprising applying an effective moisturizing amount of a personal care formulation prepared by the method of the disclosure.

In another aspect, the disclosure provides a container (e.g., a tube or jar) containing a formulation made according to the method of the disclosure, wherein instructions for application of the formulation to the skin or hair for enhancing moisturization of the skin or hair are printed on the container, on the packaging of the container, or on a document accompanying the container.

DETAILED DESCRIPTION OF THE INVENTION

Before the disclosed materials and methods are described, it is to be understood that the aspects described herein are not limited to specific embodiments, or configurations, and as such can, of course, vary. It is also to be understood that the terminology used herein is for the purpose of describing particular aspects only and, unless specifically defined herein, is not intended to be limiting.

In view of the present disclosure, the active materials and methods described herein can be configured by the person of ordinary skill in the art to meet the desired need. In general, the disclosed methods provide improvements in preparation of compositions suitable for use in personal care applications. For example, the methods of the disclosure have improved efficiency and without forming unwanted byproducts. In fact, the method of the disclosure results in a composition (i.e., a mixture of a compound of formula (I) and a polyol) that have improved moisturization efficacy on skin and/or hair. Furthermore, the combination of the compound of formula (I) and the polyol produces a synergistic relative moisturization efficacy. Thus, the combination has an increased moisturization efficacy over that expected and more than the moisturization of efficacy of the sum of the individual components. In addition, the method of the disclosure can be performed with or without catalysts, and the product composition can be used without any further purification, work-up, or distillation. Furthermore, the process uses commercially available, relatively cheap, and safe polyol ester starting materials. Polyol ester compounds, such as triacetin (1,2,3-triacetoxypropane), can also be used as humectants in personal care formulations. Thus, even if excess polyol ester compound is used in the process, it need not be removed from the resulting product composition.

One aspect of the disclosure provides a method of making a composition comprising a compound of formula (I) and a polyol, the method comprising reacting an alkanolamine of formula (II)

(II)

with a polyol ester comprising at least one —C(O)R$^1$ moiety.

In one embodiment, the polyol of the composition prepared by the method of the disclosure is derived by the cleavage of at least one —C(O)R$^1$ moiety from said polyol ester. For example, if the polyol ester is 1,2,3-triacetoxypropane (triacetin), then the resulting polyol is glycerol.

Any suitable polyol ester may be used in the methods of the disclosure and may be selected by one of skill in the art based on needs and properties of the final composition. Suitable polyol esters include, but are not limited to, triacetin, diacetin, monoacetin, acetates (e.g., monoacetates, diacetates, or mixtures thereof) of: 1,2-propanediol, 1,3-propanediol, 2-methyl-1,3-propanediol, 1,2-butanediol, 1,3-butanediol, 1,4-butanediol, 1,2-pentanediol, 1,5-pentanediol, 1,2-hexanediol, 1,6-hexanediol, and 1,2-octanediol, and acetates (e.g., mono-, di-, poly-acetates, or mixtures thereof) of: butane-1,2,3,4-tetraol, pentane-1,2,3,4,5-pentaol, and hexane-1,2,3,4,5,6-hexol (e.g., sorbitol hexaacetate), monosaccharides (e.g., D-glucose pentacetate), disaccharides (e.g., sucrose acetate isobutyrate), oligo- and polysaccharides.

In one embodiment, the polyol ester is of formula (III):

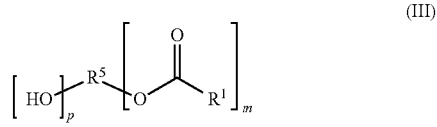

(III)

wherein
R$^1$ is an unsubstituted linear or branched C$_1$-C$_3$ alkyl;
R$^5$ is a linear or branched C$_3$-C$_6$ alkyl or a mono-, di-, oligo- or poly-saccharide sugar group;
m is an integer from 1 to 10; and
p is an integer from 0 to 9, provided that the sum of m and p is at least 2 and less than or equal to the number of carbon atoms in R$^5$.

Thus, such embodiment of the disclosure may be represented with the following chemical reaction:

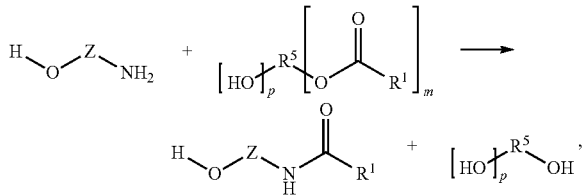

wherein Z, R$^1$, R$^5$, m and n are defined above.

The method of the disclosure may be performed without any catalyst or with catalyst. In one embodiment, the alkanolamine of formula (II) is reacted with the polyol ester in the presence of a catalyst. Such catalyst may be acid catalyst or base catalyst. Acid catalysts suitable for use in the methods of the disclosure include, but are not limited to, sulfuric acid, phosphoric acid, lactic acid and phosphorous acid. Base catalysts suitable for use in the methods of the disclosure include, but are not limited to, potassium carbonate and sodium carbonate. A catalytic amount of phosphorous acid ($H_3PO_3$) has given a nearly colorless composition.

In one embodiment, the amount of catalyst (if present) is from about 0.1 mol % to about 10 mol % based on the amount of alkanolamine of formula (II). In other embodiments, the catalyst (if present) is used in an amount from about 0.1 mol % to about 5 mol %, or about 0.1 mol % to about 2 mol %, or about 0.1 mol % to about 1 mol %, or about 0.1 mol % to about 0.5 mol %, or about 0.5 mol % to about 5 mol %, or about 0.5 mol % to about 2 mol %, or about 0.5 mol % to about 1 mol %, or about 1 mol % to about 5 mol %, or about 1 mol % to about 3 mol %, or about 1 mol % to about 2 mol %, based on the amount of alkanolamine of formula (II).

In one embodiment, the alkanolamine of formula (II) and the polyol ester are reacted without a catalyst.

The method of the disclosure may be performed in the presence or absence of a suitable solvent. Suitable solvents are preferably volatile solvents that can be easily removed, such as but not limited to methanol, ethanol, isopropanol, glycerol, propanediol, and the like. Advantageously, the method of the disclosure results in a composition that can be used without any further purification, work-up, or distillation. Thus, methods where the alkanolamine of formula (II) and the polyol ester are reacted without use of additional solvent are preferred.

In one embodiment, the molar ratio of the alkanolamine of formula (II) and the polyol ester is about X:1, wherein X is the number of —C(O)$R^1$ moieties on the polyol ester. For example, if the polyol ester is 1,2,3-triacetoxypropane (triacetin), then X is 3, and the ratio of the alkanolamine of formula (II) to 1,2,3-triacetoxypropane is about 3:1.

The polyol ester may be used in slight excess. Thus, in another embodiment, the molar ratio of the alkanolamine of formula (II) and the polyol ester is about X:1.01, or about X:1.05, or about X:1.1, or about X:1.15, or about X:1.2, or about X:1.25, wherein X is the number of —C(O)$R^1$ moieties on the polyol ester. In one embodiment, the molar ratio of the alkanolamine of formula (II) and the polyol ester is about X:1.05, wherein X is the number of —C(O)$R^1$ moieties on the polyol ester.

The method of the disclosure may be performed at temperatures suitable to carry out the reaction. In one embodiment, the reacting is carried out at a temperature of about 100° C. to about 140° C. In some embodiments, the temperature is from about 100° C. to about 130° C., or about 110° C. to about 140° C., or about 110° C. to about 130° C., or about 120° C. to about 140° C., or about 120° C. to about 130° C., or about 120° C. to about 125° C. In some embodiments, the alkanolamine of formula (II) and the polyol are reacted at a temperature of from about 120° C. to about 125° C.

The compositions prepared by the method of the disclosure comprise a compound of formula (I)

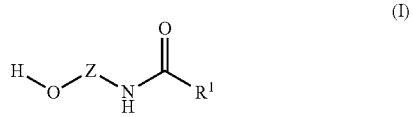

(I)

wherein
Z is (a) a linear or branched $C_2$-$C_6$ alkylene optionally substituted with one or more —OH or —($C_1$-$C_3$ alkyl)-OH, or (b) (—$R^2$—O—$R^3$—)$_n$, where n is an integer from 1 to 5, and each $R^2$ and $R^3$ is independently —$CH_2$—$CR^4H$—, wherein $R^4$ is H or an unsubstituted linear or branched $C_1$-$C_3$ alkyl; and
$R^1$ is an unsubstituted linear or branched $C_1$-$C_3$ alkyl.

The compound of formula (I) according to any embodiment herein is wherein $R^1$ is unsubstituted linear or branched $C_1$-$C_3$ alkyl. In one embodiment, $R^1$ is selected from methyl and ethyl. In another embodiment, $R^1$ is methyl.

The compound of formula (I) according to one embodiment herein is wherein Z is a linear or branched $C_2$-$C_6$ alkylene optionally substituted with one or more —OH or —($C_1$-$C_3$ alkyl)-OH. In one embodiment, Z is selected from ethylene, propylene, iso-propylene, and tert-butylene.

The compound of formula (I) according to another embodiment herein is wherein Z is (—$R^2$—O—$R^3$—)$_n$, where n is an integer from 1 to 5, each $R^2$ and $R^3$ are independently selected from —$CH_2$—$CR^4H$—, and $R^4$ is H or an unsubstituted linear or branched $C_1$-$C_3$ alkyl. In certain embodiments, n is an integer from 1 to 4. In other embodiments, n is selected from 1 or 3. In one embodiment, n is 1. In another embodiment, n is 2. In one embodiment, the compound of formula (I) is wherein $R^4$ is independently selected from H, methyl, and ethyl. In another embodiment, $R^4$ is independently selected from H and methyl. In certain embodiments, $R^4$ is independently H. In other certain embodiments, $R^4$ is independently methyl. In some embodiments, Z is —$CH_2$—$CH_2$—O—$CH_2$—$CH_2$—.

Examples of particularly useful compounds of formula (I) are

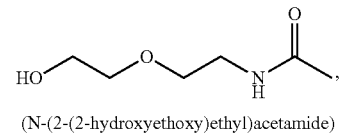

(N-(2-(2-hydroxyethoxy)ethyl)acetamide),

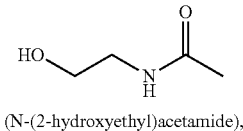

(N-(2-hydroxyethyl)acetamide),

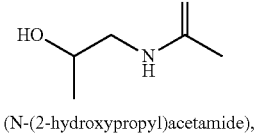

(N-(2-hydroxypropyl)acetamide),

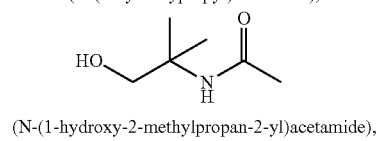

(N-(1-hydroxy-2-methylpropan-2-yl)acetamide),

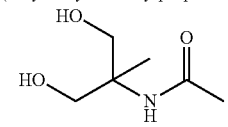

(N-(1,3-dihydroxy-2-methylpropan-2-yl)acetamide), and

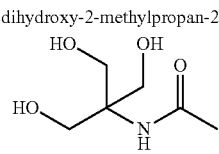

(N-(1,3-dihydroxy-2-(hydroxymethyl)propan-2-yl)acetamide).

The compound of formula (I) acts as a humectant capable of providing moisturization by, for example, retaining water.

Thus, in some embodiments, the compound of formula (I) is present in an amount sufficient to provide increased moisturization.

The compositions of the disclosure comprise a polyol. Such polyol is a byproduct and results from the polyol ester used in the process. Examples of polyols include, but are not limited to, glycerol, erythritol, xylitol, sorbitol, glucose, maltose, lactose, lactitol, sucrose, maltodextrin, and the like. In one embodiment, the polyol of the compositions of the disclosure is glycerol.

Personal care formulations comprising compositions prepared by the method of the disclosure may also include a cosmetically acceptable vehicle. While the vehicle for personal care formulations can comprise a relatively simple solvent or dispersant such as water, such vehicles can also vary greatly depending upon the type of composition (e.g., skin care or hair care) and the functionality and properties desired. For example, the cosmetically acceptable vehicle may be selected to be more conducive to topical application, including one that will form a film or layer on the skin to which the composition is applied so as to localize the application and provide some resistance to washing off by immersion in water or by perspiration. The vehicles can be creams, lotions, serums, gels, emulsions, or other liquids and can include additional ingredients such as thickening agents (such as gums) or hydrophilic colloids. The cosmetically acceptable vehicle may comprise an aqueous phase, an oil phase, an alcohol, a silicone phase or mixtures thereof. The cosmetically acceptable vehicle may also comprise an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. The emulsion may include an emulsifier, such as a nonionic, anionic or amphoteric surfactant. Suitable cosmetically acceptable vehicles and other components are well known to those skilled in the cosmetic formulation art and can be found, for example in McCutcheon's 2015 Emulsifiers and Detergents: North American Edition by Michael Allured, MC Publishing Co., 2015 edition (Mar. 2, 2015), and in McCutcheon's 2015 Functional Materials: North American Edition by Michael Allured, MC Publishing Co., 2015 edition (Mar. 2, 2015), both of which are incorporated by reference herein.

Without limitation, the cosmetically acceptable vehicle can include one or more of thickeners, surfactants, emulsifiers, suspending agents, pH adjusters and neutralizers, humectants, moisturizers, emollients, oils, waxes, solvents, chelating agents, silicones, neutralizing agents, preservatives, fragrances, dyes, pigments, conditioners, polymers, exfoliants, film formers, propellants, hair fixatives and colorants, and any combination thereof. The compound of formula (I) is compatible with most other components used in conventional personal care formulations. For example, the formulations may also contain one or more other components such as vitamins, antioxidants, botanical extracts, styling agents, antiperspirant active ingredients, anti-acne agents, anti-dandruff actives, UV filters, sunscreen actives, tanning accelerators, and other active ingredients.

Without limitation, the personal care formulations may comprise one or more ingredients selected from thickeners, surfactants, emulsifiers, suspending agents, pH adjusters and neutralizers, additional humectants, emollients, oils, waxes, solvents, chelating agents, silicones, preservatives, fragrances, dyes, pigments, conditioners, polymers, exfoliants, film formers, propellants, hair fixatives and colorants, and any combination thereof. The compound of formula (I) of the present disclosure is compatible with most other components used in conventional personal care formulations. For example, cosmetic formulations may also contain one or more other components such as vitamins, antioxidants, botanical extracts, styling agents, antiperspirant active ingredients, anti-acne agents, anti-dandruff actives, UV filters, sunscreen actives, tanning accelerators, and other active ingredients.

The CTFA Cosmetic Ingredient Handbook, Seventh Edition, 1997 and the Eighth Edition, 2000, which are incorporated by reference herein in their entirety, describe a wide variety of cosmetic and pharmaceutical ingredients commonly used in skin care formulations that are suitable for use in the formulations of the present disclosure. Examples of these functional classes disclosed in this reference include: absorbents, abrasives, anticaking agents, antifoaming agents, antioxidants, binders, biological additives, buffering agents, bulking agents, chelating agents, chemical additives, colorants, cosmetic astringents, cosmetic biocides, denaturants, depilatory compounds, drug astringents, external analgesics, film formers, fragrance components, opacifying agents, pH adjusters (such as lactic acid, citric acid, and the like), plasticizers, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, SPF boosters, insect repellants. waterproofing agents, and viscosity increasing agents (aqueous and nonaqueous).

The personal care formulations of the disclosure may include one or more thickening agents. The composition of the present invention may comprise from about 0.01% to about 10% by weight, from about 0.05% to about 1% by weight, from about 0.1% to about 0.5% by weight, or, alternatively, from about 0.1% to about 0.25% by weight, of a thickening agent or a mixture of thickening agents when present. Suitable classes of thickening agents include but are not limited to carboxylic acid polymers, polyacrylamide polymers, sulfonated polymers, copolymers thereof, hydrophobically modified derivatives thereof, and mixtures thereof. Suitable thickening agents include carboxylic acid polymers such as the carbomers (e.g., the CARBOPOL® 900 series such as CARBOPOL® 940, CARBOPOL® 954 and Carbopol ETD 2050), and Ultrez 10 and Ultrez 30 (all available from Lubrizol). Other suitable carboxylic acid polymeric agents include copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-30 alkyl acrylate crosspolymers and are commercially available as CARBOPOL® 1342, CARBOPOL® 1382, Ultrez 20, Ultrez 21, PEMULEN TR-1, and PEMULEN TR-2 (all available from Lubrizol).

The personal care formulations of the disclosure may include one or more surfactants. The formulations of the present invention may comprise from about 0.01% to about 15% by weight, from about 0.05% to about 5% by weight, from about 0.05% to about 1% by weight, from about 0.1% to about 0.5% by weight, or, alternatively, from about 0.1% to about 0.25% by weight, of a surfactant or a mixture of surfactants. The exact surfactant or surfactant mixture chosen will depend upon the pH of the composition and the other components present. Suitable surfactants include anionic, nonionic, cationic, amphoteric, or zwitterionic surfactants. The term surfactant also includes salts of fatty acids, which are typically referred to as soaps. Suitable anionic surfactants include, but are not limited to, soaps or salts of fatty acids, alkyl sulfates, alkyl ether sulfates, alpha-olefin sulfonates, alkyl aryl sulfonates, sarcosinates, alkyl glucose esters or their alkoxylates, sodium lauryl sulfate, ammonium lauryl sulfate, triethanolamine lauryl sulfate, sodium laureth sulfate, isethionates, and triethanolamine stearate. Nonionic surfactants include, but are not limited to, methyl glucose stearates or their ethoxylates, alkyl polyglucosides, and glycerol monostearate, fatty acid alkanol amides, alkyl aryl polyglycol ether, polyglycol ethers and in particular cocoyl diethanolamide, nonoxynol-7 and octoxynol-9. Exemplary cationic surfactants include, but are not limited to, mono- and di-dimethyl ammonium salts, benzalkonium chlorides, di-steary-di-methyl ammonium salts, alkyl trimethyl ammonium salts, quaternized amides of ethylene diamine, alkyl pyridinium salts, cetrimonium chloride, stearalkonium chloride and cetyl pyridinium chloride; and amphoterics including alkyl β-aminopropionates, betaines, alkyl imidazolines, cocamidopropyl betaine and caproam phocarboxy propionate.

The personal care formulations of the disclosure may include one or more emulsifiers. The formulations of the present invention may comprise from about 0.01% to about 10% by weight, from about 0.05% to about 5% by weight, from about 0.05% to about 1% by weight, from about 0.1% to about 0.5% by weight, or, alternatively, from about 0.1% to about 0.25% by weight, of an emulsifier or a mixture of emulsifiers. Exemplary emulsifiers include, but are not limited to, polyoxyethylene oleyl ether, PEG-40 stearate, ceteareth-12, Eumulgin B-1 (Henkel), ceteareth-20, Eumulgin B-2 (Henkel), ceteareth-30, Lanette (Henkel), glyceryl stearate Cutina GMS (Henkel), PEG-100 stearate, methyl myristate, isopropyl myristate, Arlacel 165, glyceryl stearate, PEG-100 stearate, steareth-2 and steareth-20, dimethicone copolyol, Polysorbate 20 (Tween 20), Polysorbate 40 (Tween 40), Polysorbate 60 (Tween 60), Polysorbate 80 (Tween 80), lauramide DEA, cocamide DEA, and cocamide MEA, Phospholipid PTC, alginate, carrageenan, Glucate DO, methylcellulose, polyvinyl alcohol, Cocamidopropyl phosphatidyl PG-dimonium chloride, stearic acid, magnesium stearate, milk amino acids, triethanolamine, and magnesium aluminum silicate.

The personal care formulations of the disclosure may also include one or more preservatives. The formulations of the present invention may comprise from about 0.01% to about 10% by weight, from about 0.05% to about 5% by weight, from about 0.05% to about 1% by weight, from about 0.1% to about 0.5% by weight, or, alternatively, from about 0.1% to about 0.25% by weight, of a preservative or a mixture of preservatives. Exemplary preservatives suitable for use in formulations of the present invention may include, but are not limited to, 5-chloro-2-methyl-1,2-thiazol-3-one, 2-methyl-1,2-thiazol-3-one, 1,3-dimethylol-5,5-dimethylhydantoin, 3-iodo-2-propynyl butyl carbamate, KATHON™ CG and GLYDANT™PLUS™, and parabens such as methylparaben and propylparaben. Additional preservatives may also be used if desired and include well known preservative compositions such as benzyl alcohol, phenyl ethyl alcohol and benzoic acid, diazolydinyl, urea, and chlorphenesin, among others.

The personal care formulations of the disclosure may also include one or more emollients. An emollient is an oleaginous or oily substance which helps to smooth and soften the skin, and may also reduce its roughness, cracking or irritation. Typical suitable emollients include mineral oil having a viscosity in the range of 50 to 500 centipoise (cps), lanolin oil, coconut oil, cocoa butter, olive oil, almond oil, macadamia nut oil, aloe extracts such as aloe vera lipoquinone, synthetic sonora jojoba oils, natural sonora jojoba oils, safflower oil, corn oil, liquid lanolin, cottonseed oil, grape seed oil, sweet almond oil, and peanut oil. Preferably, the emollient is a cocoglyceride, which is a mixture of mono, di- and triglycerides of cocoa oil, sold under the trade name of Myritol 331 from Henkel KGaA, or Dicaprylyl Ether available under the trade name Cetiol OE from Henkel KGaA or a C12-C15 Alkyl Benzoate sold under the trade name Finsolv TN from Finetex. One or more emollients may be present ranging in amounts from about 1 percent to about 10 percent by weight, preferably about 5 percent by weight. Another suitable emollient is DC 200 Fluid 350, a silicone fluid, available Dow Corning Corp.

Other suitable emollients include squalane, castor oil, polybutene, sweet almond oil, avocado oil, calophyllum oil, ricin oil, vitamin E acetate, olive oil, silicone oils such as dimethylopolysiloxane and cyclomethicone, linolenic alcohol, oleyl alcohol, the oil of cereal germs such as the oil of wheat germ, isopropyl palmitate, octyl palmitate, isopropyl myristate, hexadecyl stearate, butyl stearate, decyl oleate, acetyl glycerides, the octanoates and benzoates of (C12-C15) alcohols, the octanoates and decanoates of alcohols and polyalcohols such as those of glycol and glyceryl, ricinoleates esters such as isopropyl adipate, hexyl laurate and octyl dodecanoate, dicaprylyl maleate, hydrogenated vegetable oil, phenyltrimethicone, jojoba oil and aloe vera extract.

Other suitable emollients which are solids or semi-solids at ambient temperatures may be used. Such solid or semi-solid cosmetic emollients include glyceryl dilaurate, hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more emollients can optionally be included in the formulation.

Non-limiting examples of film forming polymers suitable for use in formulations of the present invention include but are not limited to: from Akzo Nobel Surface Chemistry LLC, Bridgewater N.J., AMPHOMER and AMPHOMER LV-71 polymers (octylacrylamide/acrylates/butylaminoethyl methacrylate compolymer), AMPHOMER HC polymer (acrylates/octylacrylamide copolymer) BALANCE 0/55, BALANCE CR and DERMACRYL AQF polymers (acrylates copolymer), BALANCE 47 polymer (octylacrylamide/butylaminoethyl methacrylate copolymer), RESYN 28-2930 polymer (VA/crotonates/vinyl neodecanoate copolymer), RESYN 28-1310 polymer (VA/Crotonates copolymer), FLEXAN polymers (sodium polystyrene sulfonate), DynamX polymer (polyurethane-14 (and) AMP-Acrylates copolymer), RESYN XP polymer (acrylates/octylacrylamide copolymer), STRUCTURE 2001 (acrylates/steareth-20 itaconate copolymer) and STRUCTURE 3001 (acrylates/ceteth-20 itaconate copolymer); from ISP, OMNIREZ-2000 (PVM/MA half ethyl ester copolymer), GANEX P-904 (butylated PVP), GANEX V-216 (PVP/hexadecene copolymer) GANEX V-220 (PVP/eicosene copolymer), GANEX WP-660 (tricontanyl PVP), GANTREZ A425 (butyl ester of PVM/MA copolymer), GANTREZ AN-119 PVM/MA copolymer, GANTREZ ES 225 (ethyl ester of PVM/MA copolymer), GANTREZ ES425 (butyl ester of PVM/MA copolymer), GAFFIX VC-713 (vinyl caprolactam/PVP/dimethylaminoethyl methacrylate copolymer), GAFQUAT 755 (polyquaternium-11), GAFQUAT HS-100 (polyquaternium-28) AQUAFLEX XL-30 (Polyimide-1), AQUAFLEX SF-40 (PVP/Vinylcaprolactam/DMAPA Acrylates Copolymer), AQUAFLEX FX-64 (Isobutylene/Ethylmaleimide/Hydroxyethylmaleimide Copolymer), ALLIANZ LT-120 (Acrylates/C1-2 Succinates/Hydroxyacrylates Copolymer), STYLEZE CC-10 (PVP/DMAPA Acrylates Copolymer), STYLEZE 2000 (VP/Acrylates/Lauryl Methacrylate Copolymer), STYLEZE W-20 (Polyquaternium-55), Copolymer Series (PVP/Dimethylaminoethylmethacrylate Copolymer), ADVANTAGE S and ADVANTAGE LCA (VinylcaprolactamNP/Dimethylaminoethyl Methacrylate Copolymer), ADVANTAGE PLUS (VA/Butyl Maleate/Isobornyl Acrylate Copolymer); from BASF, ULTRAHOLD STRONG (acrylic acid/ethyl acrylate/t-butyl acrylamide), LUVIMER 100P (t-butyl acrylate/ethyl acrylate/methacrylic acid), LUVIMER 36D (ethyl acrylate/t-butyl acrylate/methacrylic acid), LUVIQUAT HM-552 (polyquaternium-16), LUVIQUAT HOLD (polyquaternium-16), LUVISKOL K30 (PVP) LUVISKOL K90 (PVP), LUVISKOL VA 64 (PVPNA copolymer) LUVISKOL VA73W (PVPNA copolymer), LUVISKOL VA, LUVISET PUR (Polyurethane-1), LUVISET Clear (VP/MethacrylamideNinyl Imidazole Copolymer), LUVIFLEX SOFT (Acrylates Copolymer), ULTRAHOLD 8 (Acrylates/Acrylamide Copolymer), LUVISKOL Plus (Polyvinylcaprolactam), LUVIFLEX Silk (PEG/PPG-25/25 Dimethicone/Acrylates Copolymer); from Amerchol, AMERHOLD DR-25 (acrylic acid/methacrylic acid/acrylates/methacrylates); from Rohm&Haas, ACUDYNE 258 (acrylic acid/methacrylic acid/acrylates/methacrylates/hydroxyl ester acrylates from Mitsubishi and distributed by Clariant, DIAFORMER Z-301, DIAFORMER Z-SM, and DIAFORMER Z-400 (methacryloyl ethyl betaine/acrylates copolymer), ACUDYNE 180 (Acrylates/Hydroxyesters Acrylates Copolymer), ACUDYNE SCP (Ethylenecarboxyamide/AMPSA/Methacrylates Copolymer), and the ACCULYN rheological modifiers; from ONDEO Nalco, FIXOMER A-30 and FIXOMER N-28 (INCI names: methacrylic acid/sodium acrylamidomethyl propane sulfonate copolymer); from Noveon, FIXATE G-100 (AMP-Acrylates/Allyl Methacrylate Copolymer), FIXATE PLUS (Polyacrylates-X), CARBOPOL Ultrez 10 (Carbomer), CARBOPOL Ultrez 20 (Acrylates/C10-30 Alkyl Acrylates Copolymer), AVALURE AC series (Acrylates Copolymer), AVALURE UR series (Polyurethane-2, Polyurethane-4, PPG-17/IPDI/DMPA Copolymer); polyethylene glycol; water-soluble acrylics; water-soluble polyesters; polyacrylamides; polyamines; polyquaternary amines; styrene maleic anhydride (SMA) resin; polyethylene amine; and other conventional polymers that are polar solvent soluble or that can be made soluble through neutralization with the appropriate base.

Personal care formulations include, without limitation, lotions, creams (including for the face and body), rinse-off body lotions, moisturizing cleansers, soaps, anti-aging products, nourishing creams and lotions, firming and toning products, shaving creams, depilatories, deodorants, color cosmetics foundations, makeups, lipsticks, sunscreens, suntan lotions, after-sun products, personal care wipes, baby care products, bath and shower products, hair shampoo, hair leave-in conditioner, hair rinse-off conditioner, hair gel, hair lotion, hair cream, mousse, hair spray, hair dyes, hair permanent wave, hair anti-frizz, and hair volumizing products.

In one embodiment, the humectants in the personal care formulations of the disclosure consist essentially of the product of the reaction of HO—Z—$NH_2$ and a polyol ester, as described hereinabove, optionally without any purification, work-up, or distillation.

In another embodiment, the humectants in the personal care formulations of the disclosure comprise the product of the reaction of HO—Z—$NH_2$ and a polyol ester, as described hereinabove, optionally without any purification, work-up, or distillation, and another humectant.

In some other embodiments, the personal care formulation is essentially free of hydroxyethyl urea, sodium lactate, and/or sodium pyrrolidone carboxylate.

In some other embodiments, the personal care composition is essentially free of panthenol (provitamin $B_5$). As used herein the term "essentially free of," with respect to a particular ingredient, refers to the particular ingredient being present in a concentration less than is necessary for the ingredient to be effective to provide the benefit or property for which it otherwise would be used, for example, about 0.5 wt % or less, or about 0.1 wt % or less, or about 0.05 wt % or less (based on the total weight of the personal care formulation).

In another aspect, the disclosure provides a container (e.g., a tube or jar) containing a formulation comprising a composition prepared by the process of the invention and instructions for application of the formulation to the skin or hair for enhancing moisturization of the skin or hair, wherein the instructions are printed on the container, on the packaging of the container, or on a document included with the container.

In another aspect, the disclosure provides a method of moisturizing skin or hair, the method comprising applying an effective moisturizing amount of a formulation comprising a composition prepared by the method of the disclosure to the skin or hair, respectively.

Definitions

The following terms and expressions used have the indicated meanings.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an," and "the" include plural referents unless the context clearly dictates otherwise.

As used herein, the term "about" refers to the given value±10% of the value.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All percentages, ratios and proportions herein are by weight, unless otherwise specified. A weight percent (weight %, also as wt %) of a component, unless specifically stated to the contrary, is based on the total weight of the composition in which the component is included (e.g., on the total amount of the compositions). All mol % values are based on the moles of the active compounds, unless otherwise noted.

As used herein, the term "alkyl" refers to a group comprised of one to six, unless otherwise noted, saturated carbon atoms connected in a linear or branched configuration. Examples of linear alkyl groups include methyl, ethyl, n-propyl, n-butyl, n-pentyl, and n-hexyl. Examples of branched alkyl groups include iso-propyl (1-methylethyl), tert-butyl (1,1-dimethylethyl), iso-butyl (2-methylpropyl), sec-butyl (1-methylpropyl), iso-pentyl (2-methylbutyl), neo-pentyl (2,2-dimethylpropyl), iso-hexyl (2-methylpentyl, 3-methylpentyl, and 2,3-dimethylbutyl), and neohexyl (2,2-di methyl butyl).

As used herein, the term "cosmetically acceptable" means suitable for use in contact with the skin or hair of most humans and most members of lower animal species without undue toxicity, incompatibility, instability, irritation, allergic response, and the like.

As used herein, the term "polyol ester" refers to a compound comprising two or more hydroxy moieties where at least one of the hydroxy moieties is protected as an -carbonylalkyl (e.g., acetate). Examples include, but are not limited to, triacetin, diacetin, monoacetin, acetates (e.g., mono-acetates, diacetates, or mixtures thereof) of: 1,2-propanediol, 1,3-propanediol, 2-methyl-1,3-propanediol, 1,2-butanediol, 1,3-butanediol, 1,4-butanediol, 1,2-pentanediol, 1,5-pentanediol, 1,2-hexanediol, 1,6-hexanediol, and 1,2-octanediol, and acetates (e.g., mono-, di-, poly-acetates, or mixtures thereof) of: butane-1,2,3,4-tetraol, pentane-1,2,3,4,5-pentaol, and hexane-1,2,3,4,5,6-hexol (e.g., sorbitol hexaacetate), D-glucose pentacetate, and sucrose acetate isobutyrate.

As used herein, the term "sugar" means a carbohydrate comprising carbon, hydrogen, and oxygen atoms, usually with a hydrogen-oxygen atom ratio of 2:1 (e.g., with the empirical formula $C_m(H_2O)_n$ (where m and n could be the same or different). Sugars of the disclosure include monosaccharides (e.g., glucose, fructose, xylose, galactose, and the like), disaccharides (e.g., but not limited to, sucrose, lactulose, lactose, and maltose), and polysaccharides (e.g., but not limited to, maltodextrin and glycan). "Sugar' also includes hydrogenated open-chain versions of the carbohydrates mentioned above, e.g., erythritol, xylitol, sorbitol, galactitol, maltitol, lactitol, oligo- and polyglucitols, or mixtures of any of these.

EXAMPLES

The methods of the disclosure are illustrated further by the following examples, which are not to be construed as limiting the disclosure in scope or spirit to the specific procedures and materials in them.

In each of the Examples, the progress of the reaction was monitored by FT infrared spectroscopy using a Nicolet iS10 spectrometer with a single-bounce ATR accessory with ZnSe crystal and DTGS detector; the reactions were monitored for disappearance of the ester carbonyl peak in triacetin at 1739 $cm^{-1}$ and appearance of the amide carbonyl peak for the product at 1646 $cm^{-1}$.

Example 1: Preparation of MEA Acetamide

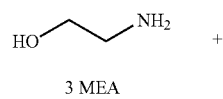

3 MEA

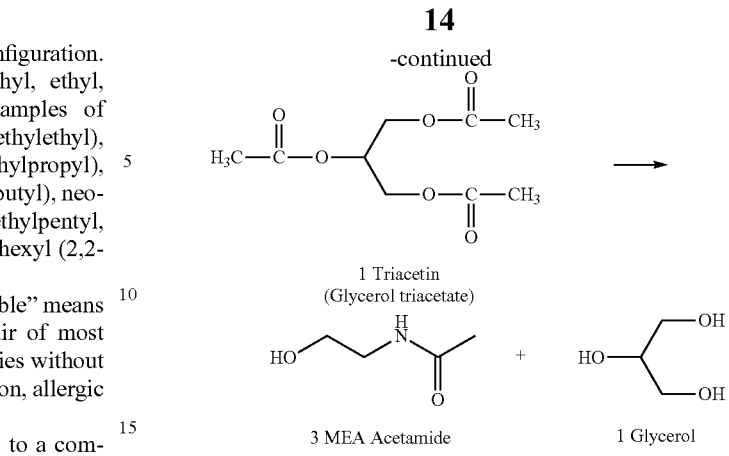

A mixture of 54.97 g (0.9 mol) of 2-aminoethan-1-ol (monoethanolamine, MEA) and 65.46 g (0.3 mol) of 1,2,3-triacetoxypropane (triacetin) was stirred and heated at about 120-125° C. in a 250 ml round bottom flask immersed in an oil bath under $N_2$ atmosphere. The mixture was stirred until the reaction showed complete conversion of triacetin to the product as monitored by FTIR. The liquid product (120.43 g) thus was obtained as a mixture of MEA Acetamide (N-(2-hydroxyethyl)acetamide) and glycerol in 3:1 molar ratio.

Example 2: Preparation of MIPA Acetamide

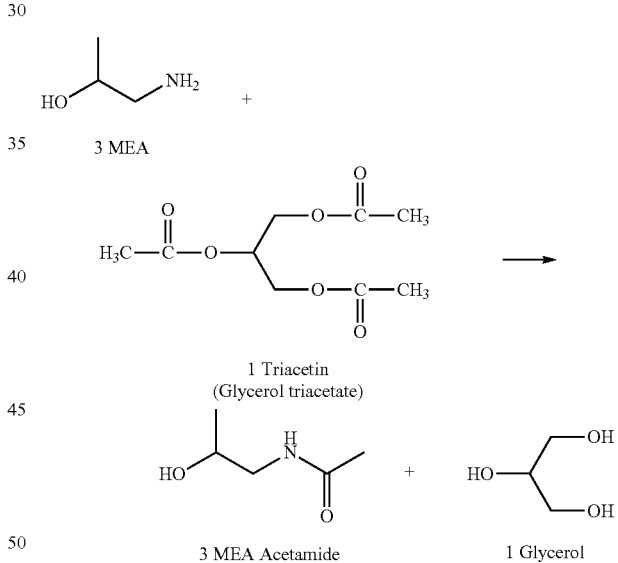

A mixture of 67.60 g (0.9 mol) 1-aminopropan-2-ol (monoisopropanolamine, MIPA), 65.46 g (0.3 mol) of 1,2,3-triacetoxypropane (triacetin), and 1.24 g (0.009 mol) of potassium carbonate was stirred and heated at about 120-125° C. in a 250 ml round bottom flask immersed in an oil bath under $N_2$ atmosphere. The mixture was stirred until the reaction showed complete conversion of triacetin to the product as monitored by FTIR. The liquid product (134.3 g) thus was obtained as a mixture of MIPA Acetamide (N-(2-hydroxypropyl)acetamide) and glycerol in 3:1 molar ratio.

Example 3: Preparation of MIPA Acetamide

The procedure in Example 2 was repeated with 1.48 g (0.018 mol) sodium carbonate used instead of potassium carbonate. The liquid product was obtained as a mixture of MIPA Acetamide (N-(2-hydroxypropyl)acetamide) and glycerol in 3:1 molar ratio.

Example 4: Preparation of AMP Acetamide

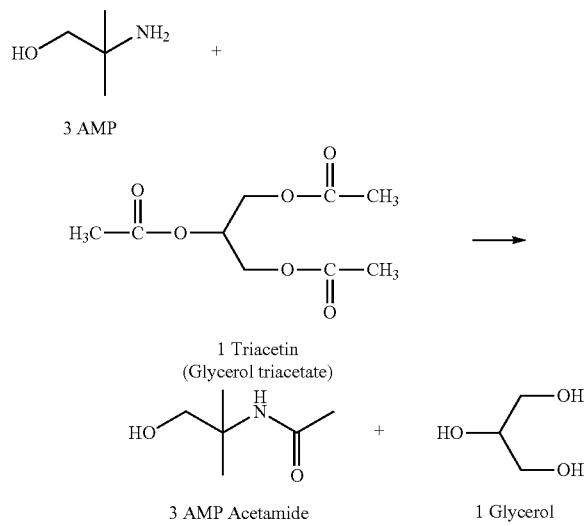

A mixture of 80.23 g (0.9 mol) 2-amino-2-methylpropan-1-ol (AMP) and 65.46 g (0.3 mol) of 1,2,3-triacetoxypropane (triacetin) was stirred and heated at about 120-125° C. in a 250 ml round bottom flask immersed in an oil bath under N$_2$ atmosphere. The mixture was stirred until the reaction showed complete conversion of triacetin to the product as monitored by FTIR. The liquid product (145.69 g) thus was obtained as a mixture of AMP Acetamide (N-(1-hydroxy-2-methylpropan-2-yl)acetamide) and glycerol in 3:1 molar ratio.

Example 5: Preparation of TRIS Acetamide

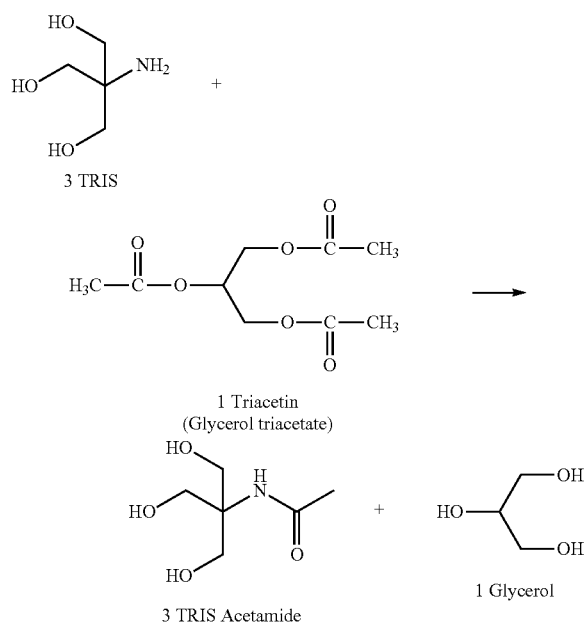

A mixture of 109.03 g (0.9 mol) 2-Amino-2-hydroxymethyl-propane-1,3-diol (TRIS) and 65.46 g (0.3 mol) of 1,2,3-triacetoxypropane (triacetin) was stirred and heated at about 120-125° C. in a 250 ml round bottom flask immersed in an oil bath under N$_2$ atmosphere. The mixture was stirred until the reaction showed complete conversion of triacetin to the product as monitored by FTIR. The liquid product (174.49 g) thus was obtained as a mixture of TRIS Acetamide (N-(1,3-dihydroxy-2-(hydroxymethyl)propan-2-yl)acetamide) and glycerol in 3:1 molar ratio.

Example 6: Preparation of DGA Acetamide

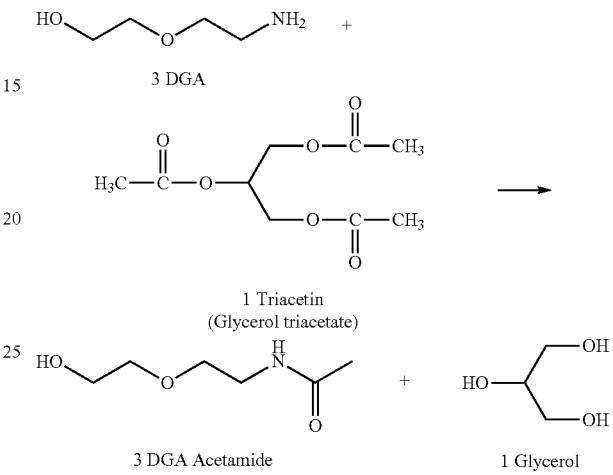

A mixture of 94.63 g (0.9 mol) 2-(2-aminoethoxy)ethanol (DGA), 65.46 g (0.3 mol) of 1,2,3-triacetoxypropane (triacetin), and 1.24 g potassium carbonate was stirred and heated at about 120-125° C. in a 250 ml round bottom flask immersed in an oil bath under N$_2$ atmosphere. The mixture was stirred until the reaction showed complete conversion of triacetin to the product as monitored by FTIR. The liquid product (161.33 g) thus obtained was a mixture of DGA Acetamide (N-(2-(2-hydroxyethoxy)ethyl)acetamide) and glycerol in 3:1 molar ratio.

Example 7: Preparation of DGA Acetamide

The procedure in Example 6 was repeated using 0.74 g (0.009 mol) phosphorous acid as a catalyst, rather than potassium carbonate. The liquid product was obtained as a mixture of DGA Acetamide and glycerol in 3:1 molar ratio.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A method of making a composition comprising a compound of formula (I)

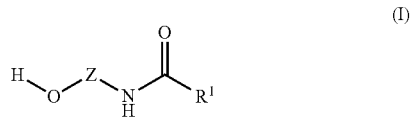

(I)

wherein

Z is (a) a linear or branched C$_2$-C$_6$ alkylene optionally substituted with one or more —OH or —(C$_1$-C$_3$ alkyl)-

OH, or (b) (—R²—O—R³—)ₙ, where n is an integer from 1 to 5, and each R² and R³ is independently —CH₂—CR⁴H—, wherein R⁴ is H or an unsubstituted linear or branched C₁-C₃ alkyl; and R¹ is an unsubstituted linear or branched C₁-C₃ alkyl; and a polyol, the method comprising reacting an alkanolamine of formula (II)

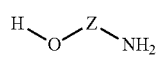

(II)

with a polyol ester comprising at least one —C(O)R¹ moiety.

2. The method of claim 1, wherein the polyol is derived by the cleavage of at least one —C(O)R¹ moiety from said polyol ester.

3. The method of claim 1, wherein the polyol ester is of formula (III):

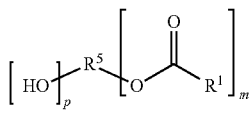

(III)

wherein
R¹ is an unsubstituted linear or branched C₁-C₃ alkyl;
R⁵ is a linear or branched C₃-C₆ alkyl or a mono-, di-, oligo or poly-saccharide sugar group;
m is an integer from 1 to 10; and
p is an integer from 0 to 9, provided that sum of m and p is at least 2 and less than or equal to the number of carbon atoms in R⁵.

4. The method on claim 1, wherein the reaction is conducted without a catalyst.

5. The method of claim 1, wherein the reaction is conducted in the presence of a catalyst.

6. The method of claim 5, wherein the catalyst is sodium carbonate, potassium carbonate, sulfuric acid, or phosphorous acid.

7. The method of claim 1, wherein the reaction is conducted without additional solvent.

8. The method of claim 1, wherein the reaction is conducted at a temperature of 100° C. to 140° C., or at 115° C. to 130° C., or at 120° C. to 125° C.

9. The method of claim 1, wherein the molar ratio of the alkanolamine of formula (II) and the polyol ester is about X:1, or about X:1.01, or about X:1.05, or about X:1.1, or about X:1.15, or about X:1.2, or about X:1.25, wherein X is the number of —C(O)R¹ moieties on the polyol ester.

10. The method of claim 1, wherein R¹ is selected from methyl and ethyl.

11. The method of claim 1, wherein Z is a linear or branched C₂-C₆ alkylene optionally substituted with one or more —OH or —(C₁-C₃ alkyl)-OH.

12. The method of claim 1, wherein Z is (—R²—O—R³—)ₙ, where n is an integer from 1 to 4, and each R² and R³ are independently selected from —CH₂—CR⁴H—, and R⁴ is H or an unsubstituted linear or branched C₁-C₃ alkyl.

13. The method of claim 1, wherein the polyol ester is 1,2,3-triacetoxypropane and the polyol is glycerol.

14. The method of claim 1, wherein the compound of formula (I) is:

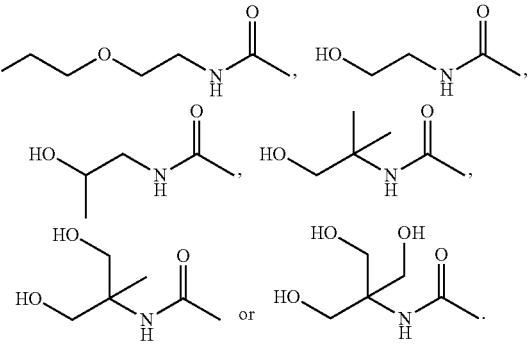

* * * * *